United States Patent [19]

Catapano

[11] Patent Number: 4,788,057

[45] Date of Patent: Nov. 29, 1988

[54] PROCESS FOR THE TREATMENT OF PSORIASIS USING TYPHOID VACCINE

[76] Inventor: Salvatore J. Catapano, 66 S. Brush Dr., Valley Stream, N.Y. 11580

[21] Appl. No.: 103,814

[22] Filed: Oct. 2, 1987

[51] Int. Cl.$^4$ .......................................... A61K 39/112
[52] U.S. Cl. ...................................... 424/92; 424/93; 435/879
[58] Field of Search ..................... 424/92, 93; 435/879

[56] References Cited

U.S. PATENT DOCUMENTS 3,035,980  5/1962  Tint et al. ......................... 424/92 X

OTHER PUBLICATIONS

Attorney's Dictionary of Medicine and Word Finder, vol.-3, p. P-301 (1986), Schmidt.
Physicians' Desk Reference (1987), p. 2209, Medical Economics Company.

Primary Examiner—Howard E. Schain
Attorney, Agent, or Firm—Roylance, Abrams, Berdo & Goodman

[57] ABSTRACT

A method of treating a human patient to effect the remission of symptoms associated with psoriasis, which comprises parenterally administering, in multiple injections, to the patient typhoid vaccine in a therapeutically effective amount which is sufficient to provide immunostimulating activity.

4 Claims, No Drawings

PROCESS FOR THE TREATMENT OF PSORIASIS USING TYPHOID VACCINE

FIELD OF THE INVENTION

This invention relates to a process for treating psoriasis by administering multiple injections of typhoid vaccine.

BACKGROUND OF THE INVENTION

Psoriasis is a chronic skin disease marked by the development of red patches on various parts of the body including elbows, back, scalp, and the hairy side of the limbs, etc. The patches are usually covered with a white scale. The cause of the disease is unknown and [heretofore] the treatment has been unsatisfactory. J. E. Schmidt, M.D., *Attorney's Dictionary of Medicine and Word Finder*, Volume 3, page P-301 (1986).

Typhoid vaccine is marketed by Wyeth Laboratories. Each c.c. contains not more than 1,000 million Salmonella Typhosa (Ty-2 strain) organisms, killed and suspended in buffered sodium chloride injection. The preservative is 0.5% phenol. It is described beginning at page 2209, Physicians'0 Desk Reference, Medical Economics Company (1987).

SUMMARY OF THE INVENTION

Suprisingly, I have discovered a method of treating a human patient which effects the remission of symptoms associated with psoriasis. The method comprises parenterally administering, in multiple injections, to the patient in need of such treatment typhoid vaccine in a therapeutically effective amount which is sufficient to provide immunostimulating activity.

DETAILED DESCRIPTION OF THE INVENTION

It has been found that a remission of the symptoms of a person afflicted with psoriasis may be achieved by the parenteral administration, in multiple injections, of typhoid vaccine in a amount of from about 0.02 to about 2.5 c.c. with no observed toxicity.

In treating for the remission of symptoms associated with psoriasis, a thorough medical history of the patient should be obtained and the patient should be given a complete physical examination. The areas of the body where psoriasis exists should be noted.

Initially, an injection of about 0.2 c.c. subcutaneously should be given to test for idiosyncrasy or existing allergy to the typhoid vaccine preparation. An allergy to the typhoid vaccine may appear as a large red spot at the area of injection. The patient should be observed for at least about 3–4 hours to determine whether there is an adverse reaction to the injection.

If there is no adverse reaction to the test injection, the patient should be started on the treatment, generally following the protocol shown in Table I.

TABLE I

Protocol for the treatment of the acquired immunedefficiency syndrome with typhoid vaccine.

Day 1 Injection of 0.2 cc subcutaneously to test for idiosincrasy or existing allergy to the typhoid vaccine preparation.
Day 4 Injection of 0.3 cc subcutaneously.
Day 8 Injection of 0.4 cc subcutaneously.
Day 12 Injection of 0.5 cc subcutaneously.
Day 16 Injection of 0.6 cc subcutaneously.
Day 20 Injection of 0.75 cc subcutaneously.
Day 24 Injection of 0.75 cc subcutaneously
Day 32 Injection of 0.75 cc subcutaneously and 0.25 cc also subcutaneously 1 hour later.
Day 40 Injection of 0.5 cc subcutaneously, 0.5 cc 1 hour later subcutaneously and 0.25½ hour later subcutaneously.
Day 48 Injection of 0.6 cc subcutaneously, 0.4 cc 1 hour later and 0.5 cc 1 hour later also subcutaneously.
Day 54 Injection of 0.5 cc subcutaneously, 0.4 cc 1 hour later and 0.6 cc 1 hour later.
Day 60 Injection of 0.4 cc subcutaneously, 0.6 cc subcutaneously 1 hour later and 0.4 cc 1 hour later subcutaneously.
Day 68 Injection of 0.75 cc subcutaneously, 0.5 cc 1 hour later and 0.25 cc 1 hour later subcutaneously.
Day 76 and every week thereafter for four weeks: 0.5 cc subcutaneously, 0.5 cc 1 hour later and then 0.25 cc subcutaneously.

It must be emphasized that the protocol listed in Table I is only a general outline of treatment in accordance with this invention. Depending on the response and clinical picture, a patient may be switched from weekly to bi-weekly injections and from single to multiple or from multiple to single injections on the day of treatment.

The patient should also be watched closely with particular attention being given to body temperature and blood pressure. An indication that the vaccine is taking effect is an elevation of body temperature within the range of about 99.6°–103° F. The immune response of the patient can be monitored using a periodic quantitative agglutination titer, e.g. a widal test should be made.

Advantageously the protocol shown in Table I is followed. Generally the protocol requires injections spaced about four (4) days apart for the first twenty four (24) days. During the first twenty four (24) days the quantity of typhoid vaccine administered is increased from about 0.3 to about 0.75 c.c. per administration. Beginning at about day thirty two (32), the patient is given a series of multiple injections, each series occurring approximately eight (8) days apart. For example, on day thirty two (32), the patient is first injected with 0.75 c.c. subcutaneously, and then one (1) hour later, is injected with 0.25 c.c. subcutaneously. Beginning at about day forty (40), a series of three (3) injections is given approximately every eight (8) days until about day seventy six (76). At day seventy six (76,) and every week thereafter for four (4) weeks, the patient receives multiple injections substantially as shown in Table I.

Once the patient is felt to have reached a stable state, a maintenance schedule can be instituted. The maintenance schedule comprises a series of multiple injections; 0.4 c.c. subcutaneously, 0.4 c.c. one (1) hour later, and 0.5 c.c. one (1) hour later, once a week until about the sixth (6) month of treatment. At that point, maintenance continues with the same series of three (3) multiple injections every other week for approximately two (2) months. By about the eighth (8) month of treatment, maintenance continues with administration every three (3) weeks, and by about the eleventh (11) month of treatment the protocol is given once (1) a month. After about fifteen months it is believed that maintenance injections can be given every three months for an indefinite period. The exact length of treatment is still undefined but after the individual becomes asymptomatic, the maintenance dose is gradually tapered and eventually discontinued. If a relapse should occur, the protocol is restarted. It should be noted that such a prolonged treatment may not be required. As seen below in Example 1, treatment may only be required for a few weeks.

It must be understood that the above-described protocol is only a general guideline and that modifications may take place at the treating physician's discretion. However, such discretion is well within the ordinary ability of a treating physician.

While the permanent eradication of psoriasis may be impossible, by a systematic course of injection of typhoid vaccine in accordance with the practice of this invention, the remission of the symptoms associated with psoriasis will continue indefinitely or the psoriasis will reach such a low level that subsequent conventional treatment, such as ultraviolet treatments, may result in 100% kill. Subsequent treatment by this process will be dependent in part on the observed response of the patient to the original protocol.

The following examples illustrate the therapeutic effect achieved by the practice of this invention.

EXAMPLE 1

A patient suffering from psoriasis began treatment using the protocol shown in in Table I. The patient had psoriasis on the legs and arms, which had persisted for many years. After approximately the fourth week of treatment with typhoid vaccine in accordance with the Table I protocol, the psoriasis was almost complete gone and the patient experienced significant relief. The patient then received a treatment using ultraviolet light and now reports almost complete disappearance of the psoriasis.

While an advantageous embodiment and example has been chosen to illustrate the invention, it will be understood by those skilled in the art that various modifications can be made therein without departing from the scope of the invention as defined in the appended claims.

What is claimed is:

1. A method of treating a human patient to effect the remission of symptoms associated with psoriasis, which comprises parenterally administering, in multiple injections, to the patient in need of such treatment typhoid vaccine in a therapeutically effective amount which is sufficient to provide immunostimulating activity.

2. The method of claim 1 where at least one subsequent administration occurs between three (3) and twenty eight (28) days after the first administration.

3. The method of claim 2 wherein more than one subsequent administration of typhoid vaccine is given, with at least one of the subsequent administrations occurring between three (3) and twenty eight (28) days after a previous administration.

4. The method of claim 1 comprising administration of typhoid vaccine substantially in accordance with Table I.

* * * * *